Jan. 21, 1958 R. G. JELLY Plant Pat. 1,675
ROSE PLANT
Filed May 20, 1957
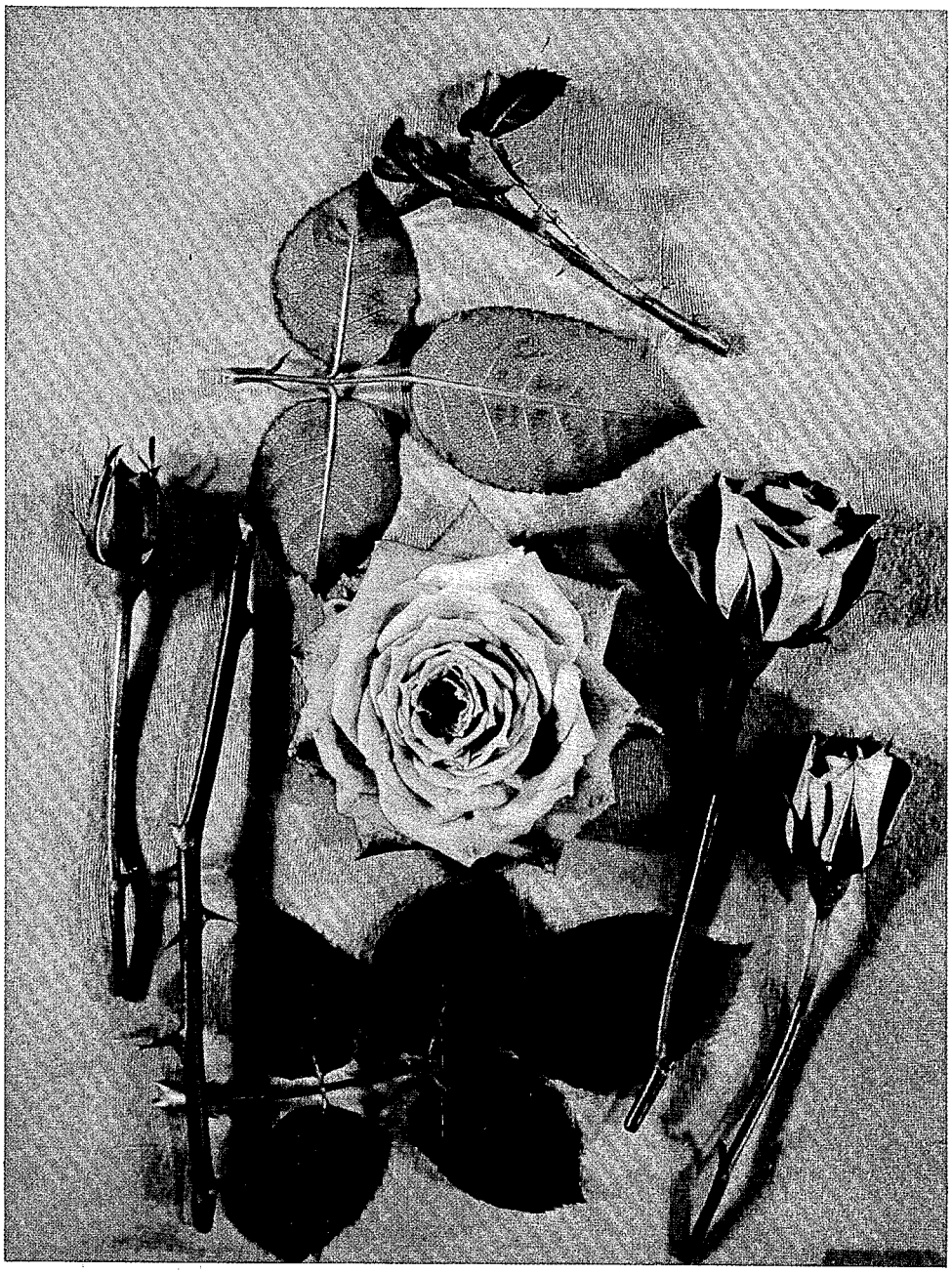
INVENTOR
R. G. Jelly
BY Robbins & Cobb
ATTORNEYS United States Patent Office Plant Pat. 1,675
Patented Jan. 21, 1958

1,675

ROSE PLANT

Robert G. Jelly, Richmond, Ind., assignor to E. G. Hill Co., Inc., Richmond, Ind., a corporation of Indiana Application May 20, 1957, Serial No. 660,434

1 Claim. (Cl. 47—61)

The present invention relates to a new and distinct variety of rose plant of the polyantha class, which was discovered by me as a sport of the variety "Stoplite" (Plant Patent No. 1,315).

The new variety was discovered by me in the greenhouses of my assignee at Richmond, Indiana, where plants of the variety "Stoplite" were being grown under my supervision and direction. At the time of my discovery, I was engaged in cutting flowers from the greenhouse plants of "Stoplite" for market purposes, and my attention was attracted to one plant in particular which exhibited a vigorous and upright growth, less clustering habit of the flowers, and more flowers of a darker and more brilliant red color than was customary of the variety "Stoplite," Upon closer observation, I found that the plant to which my attention had been attracted had sported, and I thereupon took steps to preserve the same, keep it under observation, and to later asexually reproduce the sport. These observations and asexual reproductions, as performed by grafting at Richmond, Indiana, conclusively established that the new darker color and habit of the sport were fixed and capable of being transmitted through succeeding propagations, as well as other improved and distinctive features which distinguished the new variety from its parent, "Stoplite," and from all other varieties of which I am aware.

Briefly stated, the new variety is particularly characterized as to novelty by the following outstanding features which represent a new combination in a rose of this class:

(1) A vigorous and upright habit of plant growth;
(2) Attractive foliage;
(3) Less free flower clustering habit than the parent variety;
(4) Clean free buds of exceptionally good color;
(5) Truer, darker and more brilliant red blooms than those of the parent variety; and
(6) Excellent keeping quality of the flowers.

Asexual reproduction of my new variety by grafting, as performed by me at Richmond, Indiana, shows that all of the foregoing characteristics and distinctions come true to form and are established and transmitted through succeeding propagations.

The accompanying drawing shows typical specimens of the vegetative growth and flowers of the new variety in different stages of development, and as depicted in color as nearly true as it is reasonably possible to make the same in a color illustration of this character.

The following is a detailed description of my new variety, with color terminology in accordance with Robert S. Wilson's Horticultural Colour Chart (hereinafter abbreviate as "Wilson"), Koster's Color Guide (hereinafter abbreviated as "Koster") and Ridgway's Color Standards and Nomenclature (hereinafter abbreviated as "Ridgway"), as indicated:

Type: Sport; greenhouse; for cut flowers.
Class: Polyantha.
Parentage: Sport of "Stoplite."

Propagation: Holds its distinguishing characteristics through succeeding propagations by grafting.

*Flower*

Locality where grown and observed: Richmond, Indiana.
Flowers borne: From 1 to 3 per stem; on moderately strong stems of medium length.
Quantity of bloom: Abundant, in greenhouse.
Continuity: Continuous.
Fragrance: Slight. Nature—tea.
Bud:
*Peduncle.*—Medium length; small diameter; strong; erect; almost smooth; with no thorns or prickles, but with several hairs. Color—Lettuce Green, Plate 861, pg. 176 (Wilson).
*Before calyx breaks.*—Size—small. Form—ovoid; with a conspicuous neck; with foliaceous appendages on the surface of the bud; with foliaceous parts extending beyond the tip of the bud equal to ¼ or more of its length. Color—Cress Green, Plate XXXI (Ridgway).
*As calyx breaks.*—Color—Chrysanthemum Crimson, Plate 824 (Wilson).
*As first petal opens.*—Size—medium small. Form—long-pointed. Color: outside — Chrysanthemum Crimson, Plate 824/1 (Wilson); inside—somewhat brighter than, but near Chrysanthemum Crimson, Plate 824/1 (Wilson).
*Opening.*—Opens well in greenhouse; is unaffected by hot or dry weather.
Bloom:
*Size* (when fully open).—Small; from 2¼ to 3 inches.
*Petalage.*—Double; from 35 to 50 petals; arranged regularly.
*Form.*—High-centered at first, but becoming very cupped and high-centered; petals being at first rolled inward, but becoming rolled outward later at maturity.
Petals: Moderately thin; with inside velvety and outside satiny.
*Shape.*—Outside—ovate, with apex mucronate, and with from one to several notches. Intermediate—obovate, with apex cuspidate. Inside—from ovate to obovate, with apex cuspidate.

This description of a newly opened flower was made from a rose grown in a greenhouse in the month of September, at Richmond, Indiana:

*Color.*—Outer petal: outside surface—China Rose, Plate 024 (Wilson); inside surface—slightly redder than Cardinal Red, Plate 822/2 (Wilson), with Pale Cendre Green base, Plate VI (Ridgway). Intermediate petal: outside surface—China Rose, Plate 024/1 (Wilson); inside surface—slightly darker than Rose Red, Plate 724 (Wilson). Inner petal: outside surface—Indian Lake, Plate 826/1 (Wilson); inside surface—Indian Lake, Plate 826 (Wilson).

This description was made from a rose that was open for three days in a greenhouse in the month of September, at Richmond, Indiana:

*Color.*—Outer petal: outside surface—Rose Red, Plate 724/1 (Wilson); inside surface—much darker than Rose Red, Plate 724 (Wilson). Intermediate petal: outside surface—Rose Red, Plate 724/3 (Wilson); inside surface—Rose Red, Plate 724 (Wilson). Inner petal: outside surface—Rose color, Plate XII (Ridgway); inside surface—slightly darker than Rose Red, Plate 724 (Wilson).
*General color effect.*—Newly opened flower—Cardinal Red, Plate 722/1 (Wilson). 3-days open—Rose Red, Plate 724 (Wilson).

*Flower longevity.*—Cut roses grown in greenhouse and kept at living-room temperatures—7 days in April.

*Plant*

Foliage:

*Leaves.*—Compound of 3, 5 or 7 leaflets; normal abundance; medium size; moderately leathery.

*Leaflets.*—Shape—ovoid, with apex acute. Base—from round to acute. Margin—serrate.

*Color.*—Mature: upper surface—Empire Green, Plate XXXII (Ridgway); under surface—Lavender Green, Plate 000761 (Wilson). Young: upper surface—Hay's Maroon, Plate XIII (Ridgway); under surface—Dark Violet, Plate 58 (Koster).

*Rachis (the supporting stem of the compound leaf).*—From light to medium. Upper side—grooved; slightly prickly. Under side—almost smooth.

*Stipules.*—Short; narrow; with points of medium length turning out at an angle of less than 90°; recurved slightly toward the stem.

Growth:

*Habit.*—Upright; much-branched.

*Growth.*—Free; vigorous.

*Canes.*—From small to medium diameter.

*Main stems.*—Color—Cress Green, Plate XXXI (Ridgway). Thorns — several; short; hooked slightly downward; with long, narrow base; color Snuff Brown, Plate XXIX (Ridgway). Prickles—none. Hairs—none.

*Branches.*—Color—Spinach Green, Plate 0960/1 (Wilson). Thorns — several; medium length; some straight and some hooked slightly downward; with narrow base; color—varying from Dark Olive Buff, Plate XL (Ridgway), to Army Brown, Plate XL (Ridgway). Prickles—none. Hairs—none.

*New shoots.*—Color—Spinach Green, Plate 0960/2 (Wilson). Thorns — Several; medium length; hooked downward; with narrow base; color—Corinthian Red, Plate XXVII (Ridgway). Prickles—none. Hairs—none.

*Reproductive organs*

Stamens: Medium number; arranged regularly about pistils; tucked in calyx.

Filaments: Short; many; most with anthers. Color—Pale Pinkish Buff, Plate IV (Ridgway).

Anthers: Medium size; all open at once. Color—Pinkish Cinnamon, Plate XXIX (Ridgway).

Pollen: Moderate abundance. Color—Apricot Yellow, Plate IV (Ridgway).

Pistils: Medium number.

Styles: Uneven; medium length; moderately thin; bunched; columnar. Color—Pale Dull Green-yellow, Plate XVII (Ridgway).

Stigma: Color—Pale Chalcedony Yellow, Plate XVII (Ridgway).

Ovaries: Some protruding from calyx.

Hips: Short; flat-top; pointed base; with conspicuous, very smooth, gourd-shaped neck; walls thin and fleshy. Color—Persimmon Orange, Plate 7/0 (Wilson).

Sepals: Permanent; medium length; spear-shaped; recurved. Color: inside—Lavender Green, Plate 000761 (Wilson); outside—Willow Green, Plate 000862 (Wilson).

Seeds: Few; from small to medium size.

I claim:

A new and distinct variety of rose plant of the polyantha class, substantially as herein shown and described, characterized particularly as to novelty by its vigorous and upright habit of plant growth, its attractive foliage, its reduced cluster habit, its clean, free buds of exceptionally good color, its dark and brilliant red blooms, and the excellent keeping quality of its blooms as cut flowers.

No references cited.